United States Patent [19]

Nic

[11] Patent Number: 5,431,654
[45] Date of Patent: Jul. 11, 1995

[54] BONE CEMENT INJECTOR

[75] Inventor: David M. Nic, Portage, Mich.

[73] Assignee: Stryker Corporation, Kalamazoo, Mich.

[21] Appl. No.: 769,003

[22] Filed: Sep. 30, 1991

[51] Int. Cl.⁶ .................................................. A61F 2/32
[52] U.S. Cl. ...................................... 606/92; 606/93
[58] Field of Search ................................ 606/92–94; 604/61, 209; 222/391

[56] References Cited

U.S. PATENT DOCUMENTS

| | | |
|---|---|---|
| D. 261,425 | 10/1981 | Bruhn . |
| 546,073 | 9/1895 | Mix . |
| 2,224,967 | 12/1940 | Kaye . |
| 2,732,102 | 1/1956 | Ekins . |
| 2,750,943 | 6/1956 | Dann . |
| 2,778,541 | 1/1957 | Sherbondy . |
| 2,838,210 | 6/1958 | Detrie et al. . |
| 3,058,632 | 10/1962 | Stremmel . |
| 3,112,743 | 12/1963 | Cochran et al. . |
| 3,141,583 | 7/1964 | Mapel et al. . |
| 3,160,156 | 12/1964 | Tyler . |
| 3,193,146 | 7/1965 | Isgriggs et al. . |
| 3,255,747 | 6/1966 | Cochran et al. . |
| 3,368,592 | 2/1968 | Thiel et al. . |
| 3,422,814 | 1/1969 | Lloyd . |
| 3,721,229 | 3/1973 | Panzer . |
| 3,739,947 | 6/1973 | Baumann et al. . |
| 3,765,413 | 10/1973 | Lepar . |
| 3,815,878 | 6/1974 | Baskas et al. . |
| 3,894,663 | 7/1975 | Carhart . |
| 3,907,106 | 9/1975 | Purrmann et al. . |
| 4,090,639 | 5/1978 | Campbell ............................ 222/43 |
| 4,274,163 | 6/1981 | Malcom et al. . |
| 4,277,184 | 7/1981 | Solomon . |
| 4,338,925 | 7/1982 | Miller . |
| 4,405,249 | 9/1983 | Scales ................................... 606/93 |
| 4,546,767 | 10/1985 | Smith ................................... 606/93 |
| 4,576,152 | 3/1986 | Müller ................................. 606/93 |
| 4,671,263 | 6/1987 | Draenert ............................. 606/93 |
| 4,787,751 | 11/1988 | Bakels . |
| 4,815,454 | 3/1989 | Dozier, Jr. . |
| 4,973,168 | 11/1990 | Chan .................................. 366/139 |
| 4,994,065 | 2/1991 | Gibbs ................................... 606/92 |
| 5,052,243 | 10/1991 | Tepic ................................... 606/92 |

Primary Examiner—Michael A. Brown
Attorney, Agent, or Firm—Flynn, Thiel, Boutell & Tanis

[57] ABSTRACT

Apparatus for injecting bone cement from a cartridge in orthopedic surgery having a body and structure supporting a bone cement containing cartridge on the body. A trigger structure is actuable for movement on the body. Ram structure is advanceable on the body in response to actuation of the trigger structure for forcing bone cement from the cartridge toward a surgical site. Structure interposed between the trigger structure and ram structure is actuable for changing, between a lower force value and a higher force value, the force appliable by the ram to the cartridge in response to a given actuation of the trigger structure.

25 Claims, 5 Drawing Sheets

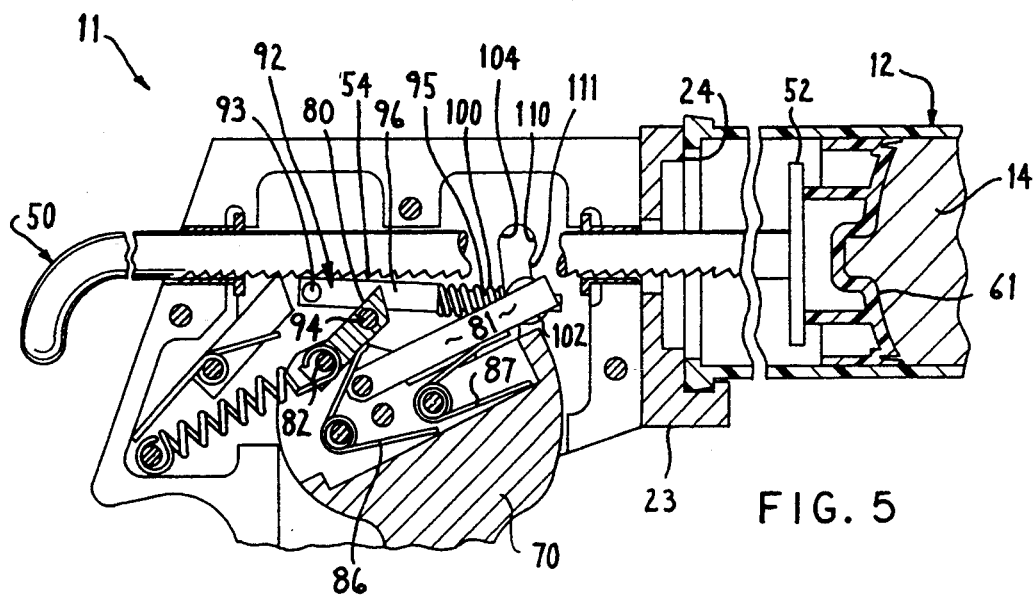
FIG. 5
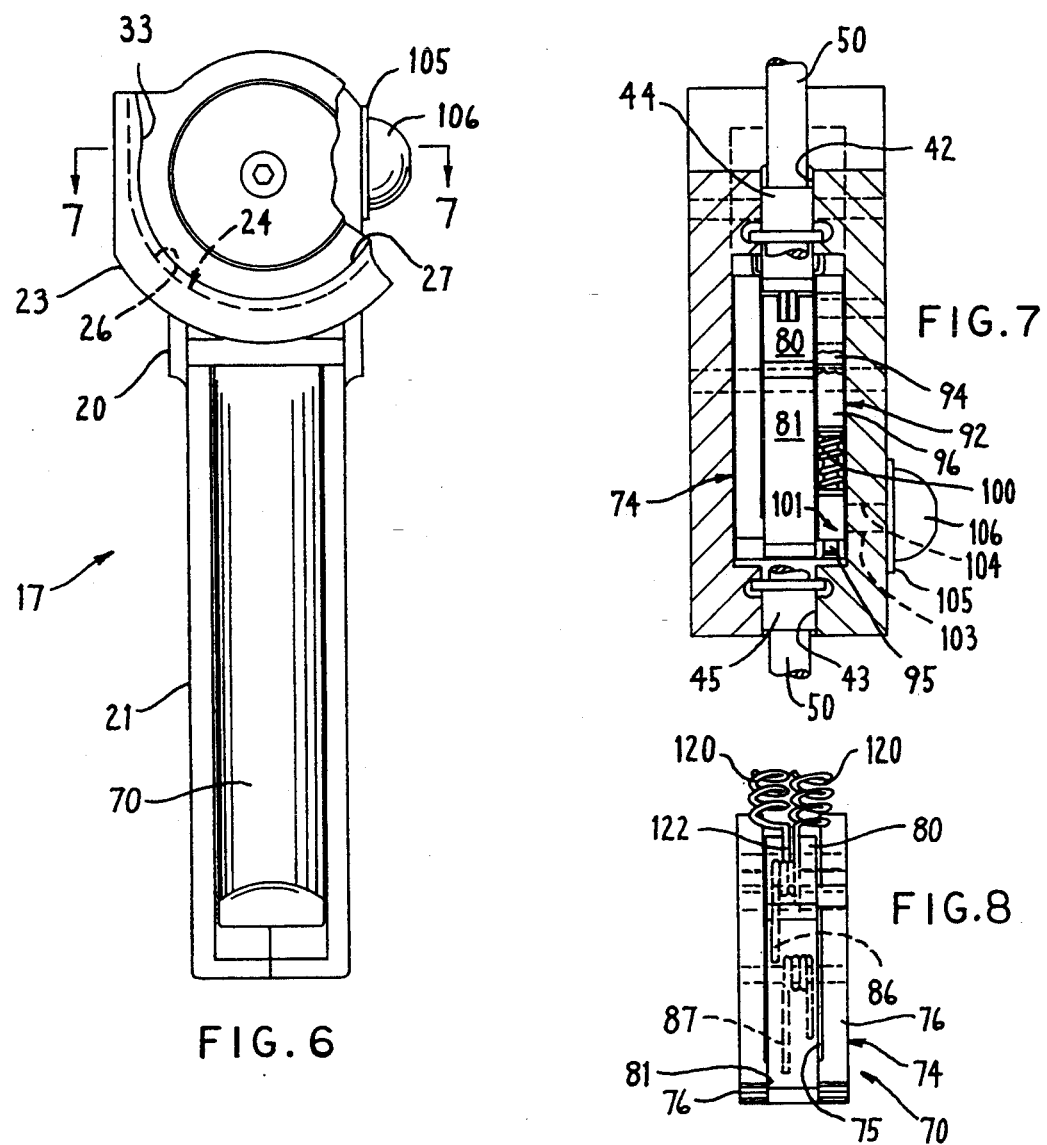
FIG. 6
FIG. 7
FIG. 8

BONE CEMENT INJECTOR

FIELD OF THE INVENTION

This invention relates to apparatus for injecting bone cement under pressure onto bone, or into a bone cavity, during a surgical procedure.

BACKGROUND OF THE INVENTION

It is known to apply bone cement to bone in orthopedic surgical procedures. For example, as part of the installation of an artificial hip joint, the top of the femur is removed and bone cement is packed into the exposed top of the femoral cavity, whereafter the stem of the hip joint prosthesis can be inserted into the top of the femoral cavity to be held in place therein upon curing of the cement, which bonds to the prosthesis stem and to the bone as well.

It has been known to pack bone cement into the femoral cavity by hand.

A major disadvantage of this procedure is that it tends not to apply sufficient pressure to the cement in the cavity, so that the cement tends not to adequately penetrate the pores of the bone within the femoral cavity and thus produces a bond with the femur which is weaker than desired.

Further, this prior procedure is excessively time consuming, which is particularly disadvantageous with two-part bone cements which cure (harden) quickly and so may harden prematurely, i.e. before the surgeon has time to finish packing the femoral cavity.

Further, packing bone cement into the femoral cavity tends to trap air bubbles in the cement packed into the femoral cavity, resulting in unwanted voids in the cement which weaken the bond between the implant stem and femur.

Further, as a result of factors including those above discussed, the quality of the cement bond tends to vary widely from surgeon to surgeon and between subsequent patients of the same surgeon.

In an attempt to overcome some of these disadvantages of hand packing, several companies now offer mechanical bone cement insertion devices which are broadly reminiscent of the common household caulking gun and cartridge. Typically, these prior bone cement injection devices have a pistol-shaped body for releasably supporting a forward extending cartridge containing bone cement and having a ram actuable by a manually movable trigger for pushing bone cement out the front of the cartridge through a suitable nozzle and into the femoral cavity.

In such prior guns the ram is driven by an elongate rod slidable coaxially toward the cartridge forcibly ejecting cement from the forward end of the cartridge. Pulling the trigger typically acts through a pawl engaging rack teeth distributed lengthwise on the rod to advance the ram, or moves a jam washer into jamming engagement with a smooth rod to advance the rod, and hence the ram. In either case, a series of pulls of the trigger results in a series of advancements of the rod and dispensing of corresponding portions of the cement mixture from the front end of the cartridge.

In some prior guns of this kind, structures are provided for adjusting the dispensed quantity of cement mixture, per trigger pull. However, in such prior devices of which I am aware, this is accomplished by relocating a trigger abutting member to different positions on the gun body, to prevent pulling of the trigger beyond any of several selected points along its path of movement, i.e. to prevent pulling the trigger through its full path.

However, this prior adjustment serves merely to change the volume of cement dispensed per trigger pull. It does not, for example, change the ratio of the force applied to the trigger with respect to the pressure applied by the ram to the bone cement within the cartridge.

Presently popular two-part bone cements which must be mixed and injected quickly, having a curing cycle of perhaps 6 to 8 minutes, for passing from a free flowing liquid state (similar to a syrup or watery pancake batter in consistency) to a putty-like consistency and finally to a hard rigid block. Such prior gun/cartridge devices are used by repetitively pulling the gun trigger to inject, over time, the required total amount of cement into the femoral cavity, during which time the mixed cement continues to stiffen. Moreover, filling a femoral cavity with bone cement first calls for injection of a substantial volume of cement to substantially fill the cavity, followed by application of pressure to the exposed end of the cement column to try to press the cement into the pores of the bone surrounding the femoral cavity. Applicant has noted a relation between the two phenomena immediately above stated, namely the tendency of the cement to be more free flowing during initial filling of the femoral cavity and the tendency of the cement to be stiffer at the end of the filling process when it is desired to provide additional pressure on the cement in the cavity.

Accordingly, the objects and purposes of the present invention include provision of an apparatus for injecting bone cement from a cartridge in orthopedic surgery; in which the operator can switch between dispensing a relatively high volume of bone cement at a relatively low pressure, and dispensing a relatively low volume of bone cement at a relatively high pressure without changing the force applied to the trigger or the displacement of the trigger per trigger pull; in which the operator can elect to dispense in the high volume, low pressure mode while the cement is still easily flowable or before the surgical site (for example a femoral cavity) is near to being filled; in which the operator can elect to use the low volume, high pressure mode after the stiffness of the cement increases during curing and/or while, for example, dispensing the last increment of cement into the femoral cavity while pressing same into the pores in the bone surrounding the cavity; in which the apparatus is freely shiftable back and forth between high pressure/low volume and low pressure/high volume modes by means of a simple control actuable by the finger of the user outside the gun; and in which the change in mode involves a change in the driving connection from the trigger to the rod.

Further objects and purposes of the invention will be apparent to persons acquainted with apparatus of this type upon reading the following specification and inspecting the accompanying drawings.

One aspect of the present invention can be defined as follows. Apparatus for injecting bone cement from a cartridge in orthopedic surgery comprises a body, means for supporting a bone cement containing cartridge on the body, trigger means actuable for movement on the body, ram means advanceable on the body in response to actuation of the trigger means for forcing bone cement from the cartridge to the surgical site, and means operatively interposed between the trigger means and ram means and actuable for changing, between a lower force value and a higher force value, the force appliable by the ram means to the cartridge in response to a given actuation of the trigger means.

BRIEF DESCRIPTION OF THE DRAWINGS

FIG. 5 is a view similar to FIG. 4 and showing the apparatus in its high force, low displacement mode.

FIG. 6 is a partially broken front elevational view of the FIG. 3 apparatus.

FIG. 7 is a sectional view substantially taken on the line 7—7 of FIG. 6.

FIG. 8 is a top view of the trigger of FIG. 3.

DETAILED DESCRIPTION

Figure 1:
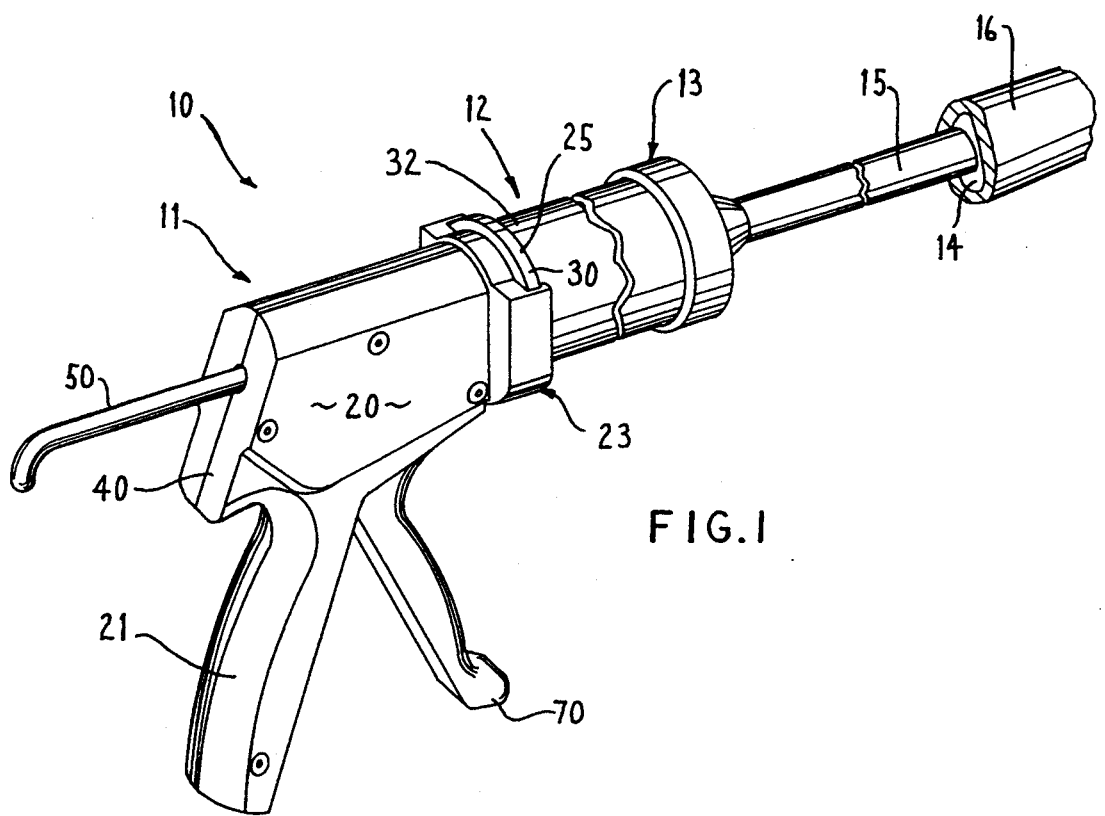
FIG. 1 is a pictorial view of an apparatus embodying the invention shown in one example of a position of use, injecting bone cement into the end of a hollow bone such as a femur.

FIG. 1 discloses an apparatus 10 embodying the invention. The apparatus 10 comprises a generally pistol shaped device, hereafter conveniently referred to as a gun 11, on which is removably supported a cartridge 12. The cartridge 12 contains bone cement and has on its forward end a dispensing nozzle 13 of any convenient type, for convenient example, having a forwardly extending tip 15 inserted into the surgically opened upper end of a femur 16 of a patient (not shown), for filling same with bone cement 14 preparatory to installation of the stem of an artificial hip replacement prosthesis (not shown) therein.

The gun 11 (FIG. 2) includes a body 17 comprising a hollow forward extending receiver 20 from the lower rear portion of which depends an integral handle 21. In the particular embodiment shown, and for convenience in construction, the body 17 is formed of opposed left and right halves, held together by transverse screws 22.

A cartridge support 23 is fixed to the front end (right end in FIG. 2) of the receiver 20 by screws 24. The cartridge support 23 is a generally puck-shaped member having rounded perimeter portions at top and bottom and having a forward and upward opening recess 25. The recess 25 has an upward opening generally U-shaped perimeter wall 26 (FIGS. 2, 3 and 6) which is closed downward and sideward and opens freely upwardly and is of forward extending cylindrical form. A correspondingly oriented, generally U-shaped, radially inward extending flange 27 guards the front end of the recess 25 at the bottom and sides thereof, the flange 27 not extending across the top of the recess 25.

Figure 4:
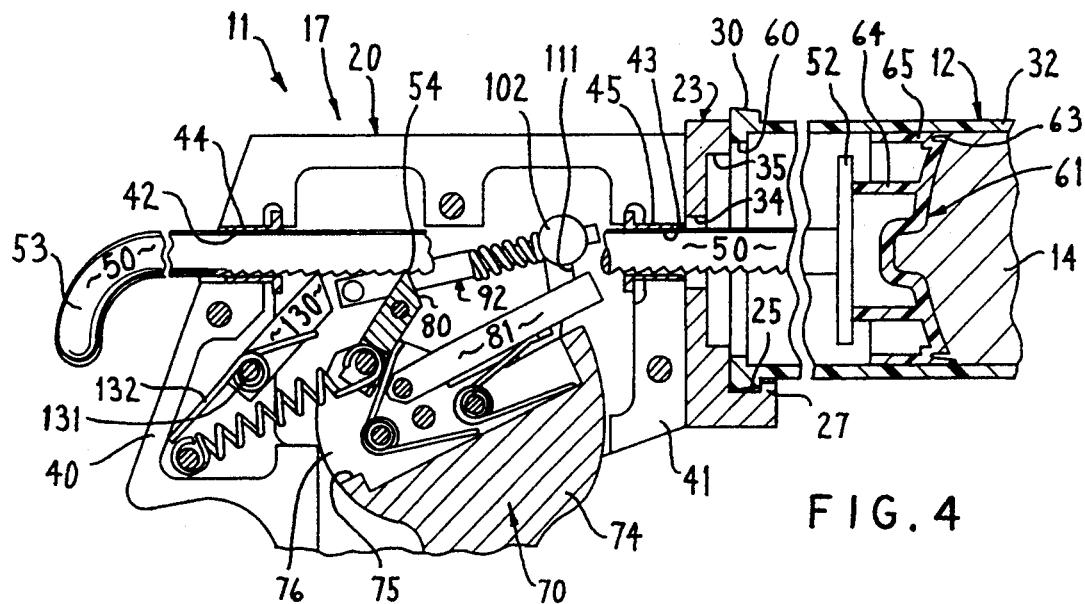
FIG. 4 is a fragment of FIG. 3 showing the rod in a forwardly advanced position and with the apparatus in its large displacement, low force mode.
Figure 3:
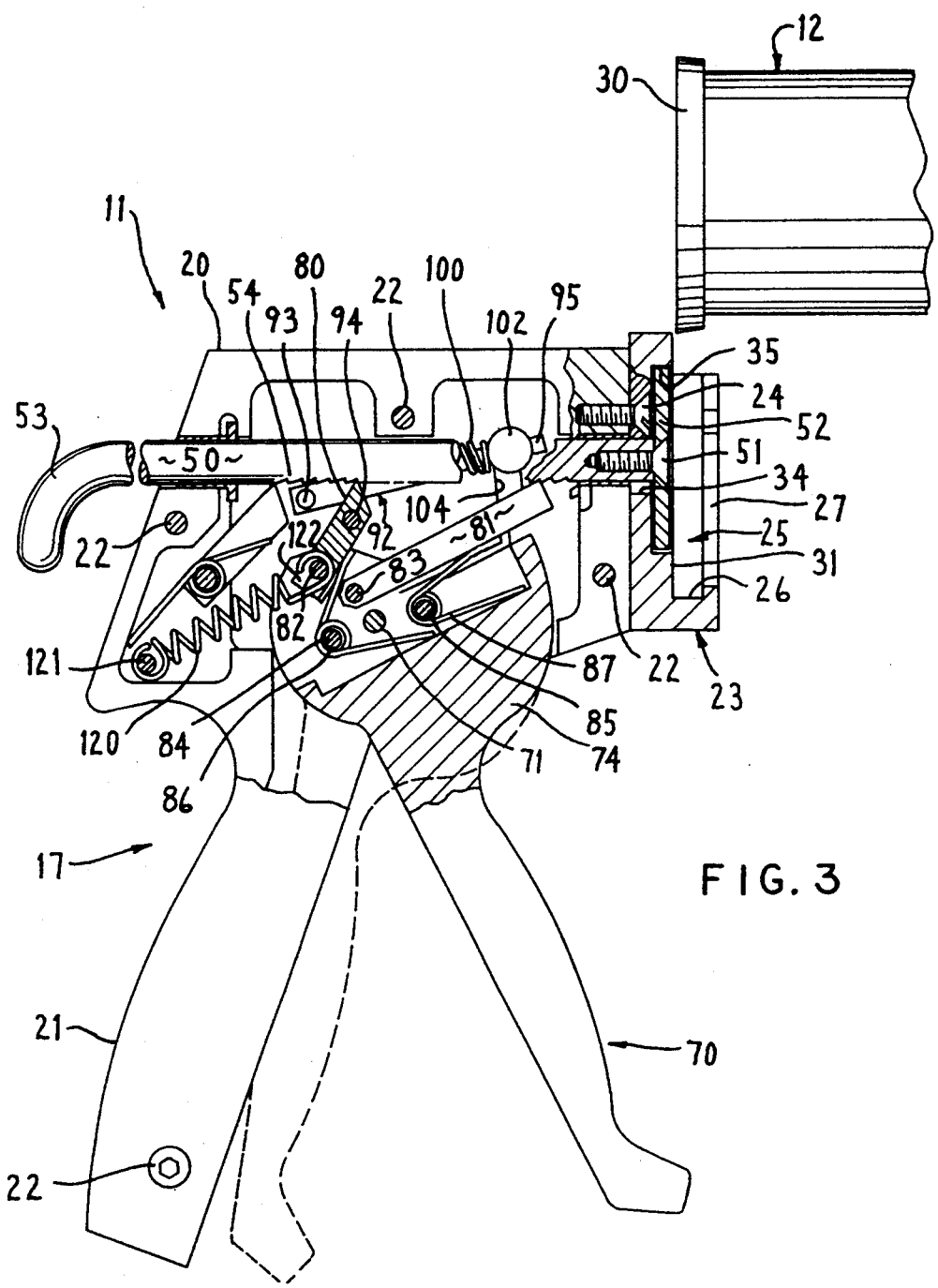
FIG. 3 is a fragmentary, side elevational view, partially in central cross section, of the FIG. 1 gun, showing alternative unpulled and fully pulled positions of the trigger in solid and broken lines, respectively.
Figure 9:
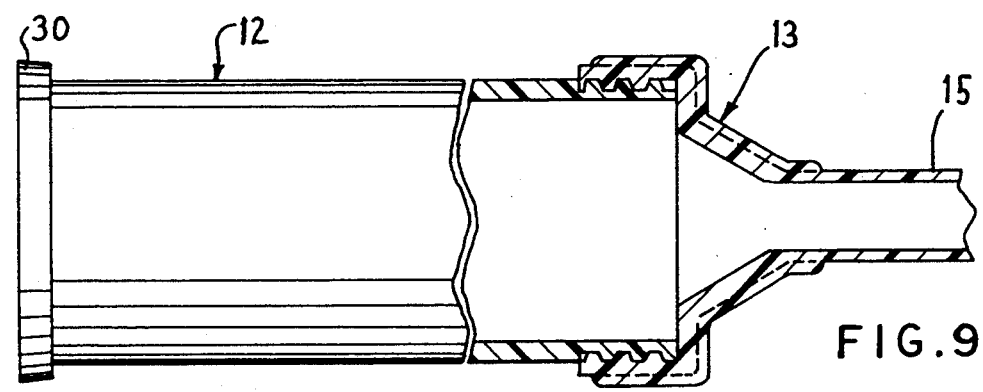
FIG. 9 is a fragmentary, partially broken top view of the cartridge and outlet nozzle of FIG. 1.

The cartridge 12 has a radially outward extending flange 30 (FIGS. 1, 3 and 9) circumferentially surrounding the rear end thereof. To releaseably fix the cartridge 12 in forward extending, cantilevered relation on the front end of the gun 11, as shown in FIG. 1, the rear end portion of the cartridge 12 is dropped into the cartridge support recess 25 from above. FIG. 3 shows the cartridge 12 just prior to such dropping in. FIGS. 1 and 4 show the cartridge 12 after completion of such dropping in. More specifically, the cartridge rear flange 30 is snugly but slidably received down into the cartridge support recess 25 so as to be bounded at its sides and lower portion by the recess perimeter wall 26. The recess flange 27 thus blocks positively the ability of the cartridge 12 to move forward out of the cartridge support recess 25. Indeed, the cartridge rear flange 30 is snugly but upwardly slidably sandwiched axially between the recess flange 27 in front thereof and the end wall 31 (leftward end in FIG. 3) of the cartridge support recess 25.

The recess flange 27 snugly but upwardly slidably surrounds the perimeter wall 32 of the cartridge immediately ahead of the cartridge flange 30. As seen from the front in FIG. 6, the cartridge support flange 27 is of slightly more than 180° circumference, so as to form a horizontally opposed pair of small ears 33 (only one of which is shown in FIG. 6) symmetrically arranged into the upper end of the U-shaped, upwardly opening recess flange 27 to form a resiliently overcome, snap fit latch for positively but resiliently releasably holding the cartridge 12 against upward movement in the cartridge support recess 25. In other words, the opposed ears 33 very slightly overlie the upper half of the perimeter wall 32 of the cartridge 12 so that a small resilient "give" of the ears 33 and/or perimeter wall 32 of the cartridge 12 is required to push the cartridge 12 down into, or pull the cartridge 12 up out of, the cartridge support recess 25.

A rear opening, central through hole 34 (FIGS. 3 and 4) extends from the recess 25 rearward through the rear surface of the cartridge support 23. Indeed, a forward facing, shallow, circular secondary recess 35 coaxially communicates between the through hole 34 and the above-described cartridge flange receiving recess 25. The through hole 34 and recesses 35 and 25 are coaxial with a cartridge 12 installed in the cartridge support 23 in the manner shown in FIGS. 1 and 4.

The receiver 20 has rear and front walls 40 and 41. Holes 42 and 43 extend through the rear and front walls 40 and 41 respectively and are coaxial with the hole 34 and recesses 35 and 25 in the cartridge support 23 and thus with the cylindrical perimeter wall 32 of a cartridge 12 properly installed in the cartridge support as shown in FIG. 4. Bushings 44 and 45 (FIGS. 2 and 4) fixedly line the respective holes 42 and 43 and are radially flanged to cooperate with the interior wall of the receiver in such way as to prevent the bushings 44 and 45 from escaping from the holes 42 and 43 respectively.

A ram rod 50 (FIGS. 2 and 4) extends snugly but slidably through the bushings 44 and 45 and thence loosely through the central hole 34 of the cartridge support 23. Coaxially fixed to the front end of the rod 50, here by a coaxial screw 51, is a ram disk 52. The rear end of the rod 50 is bent to form a finger grip 53 (FIG. 4) for manually pulling the rod 50 rearward to its rearwardmost position in FIG. 3. The rod 50 is of circular cross section and is rotatable within the bushings 44 and 45 to reposition it circumferentially with respect to the receiver 20. In its position shown in FIG. 4, with the finger grip 53 pointed downward, the underside of the rod 50, throughout its major length, is provided with a series of evenly axially spaced, transversely extending teeth 54 defining a rack. The teeth 54 each have a substantially radial face engageable by pawls hereafter discussed and a ramplike, sloped front face which allows the rod 50 to be manually pushed forward over such pawls without interference.

In its rearward position shown in FIG. 3, the ram disk 52 is fully recessed in the secondary recess 35 of the cartridge support 23, so as not to interfere with loading of the rear end flange 30 of a cartridge 12 downward into the primary recess 26 of the cartridge support 23 (note the transition downward of the cartridge from FIG. 3 to FIG. 4).

The rear end of the cartridge 12 is open except for a small radially inwardly extending flange 60 (FIG. 4). The cartridge contains a piston 61 snugly and sealingly and axially movable within the cylindrical perimeter wall 32 of the cartridge 12. Normally a quantity of bone cement 14 has been loaded into the cartridge 12 ahead of and bearing on the front face of the piston 61. The small radially inward extending flange 60 at the rear end of the cartridge 12 radially overlaps the perimeter skirt 65 of the piston 61 and prevents the piston 61 from escaping through the rear end of the cartridge. The piston 61 has an annular feather seal 63 to prevent escape of cement 14 rearwardly therepast and to enable forward movement of the piston 61 to displace such bone cement 14 out the front of the cartridge 12 and through the nozzle 13 as above described with respect to FIG. 1. The piston 61 has a coaxial annular flange 64 (FIG. 4) which extends rearward past the perimeter skirt 65 of the piston. The annular flange 64 is radially spaced intermediate the perimeter flange 65 and the center of the piston 61 and is of diameter somewhat smaller than the ram disk 52. Upon sufficient forward advancement of the rod 50, the ram disk 52 abuts the annular flange 64 of the piston and moves the piston forwardly and thereby moves the bone cement 14 in the cartridge 12 forwardly out of the nozzle 13.

A trigger 70 is pivoted at its upper end on a transverse pin 71 (FIGS. 2 and 3) in turn fixed at its ends in holes (one being shown at 72 in FIG. 2) in the opposed faces of the left and right halves 17L and 17R of the gun body 17. Washers 73 (FIG. 2) are opposed between the upper end of the trigger 70 and the opposed left and right halves of the gun body 17 to act as simple axial thrust bearings and thereby allow free pivoting of the trigger 70 with respect to the body 17. The trigger 70 is thus pivotable between a front position (the rest position) shown in solid lines in FIG. 3 and a rear position (the fully pulled position) shown in dotted lines in FIG. 3.

Figure 2:
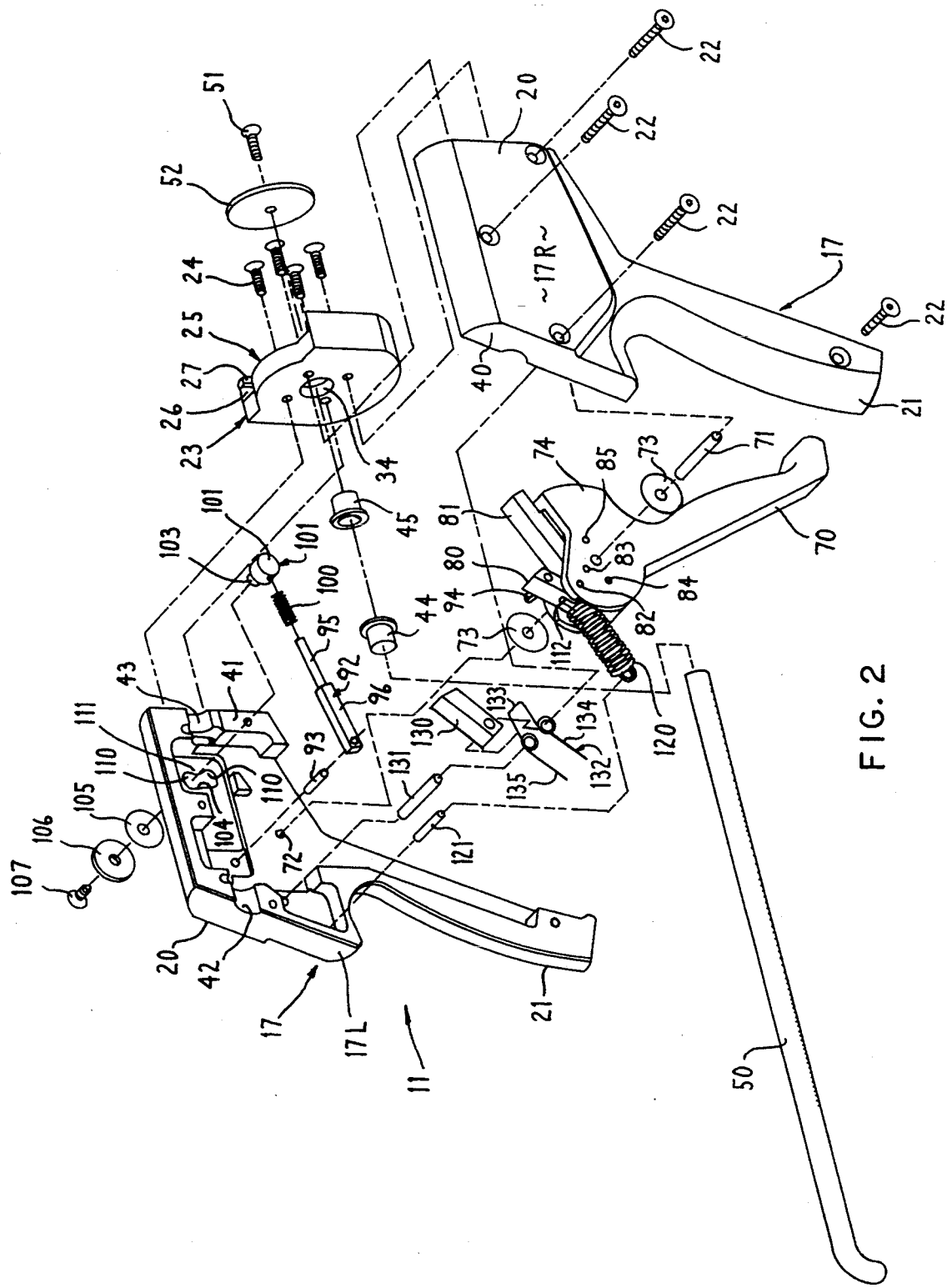
FIG. 2 is an exploded pictorial view of the gun of FIG. 1.

In the embodiment shown, the upper end of the trigger 70 is formed as a head 74 which is enlarged in the forward and rearward directions and is pivoted on the pivot pin 71. As seen in FIGS. 2, 3 and 8, the trigger head 74 is provided with an upward and rearward opening groove 75. The upper part of the trigger head 74 comprises upstanding cheeks 76 which are transversely opposed across the groove 75. The groove 75 serves to house drive pawls 80 and 81, hereafter referred to as low force/large displacement pawl 80 and high force/low displacement pawl 81.

Pawl pivot pins 82 and 83 extend transversely across the groove 75 and have opposite ends fixedly supported by respective ones of the opposed cheeks 76 for pivotally supporting the lower, rearward ends of the pawls 80 and 81 respectively. In general, the pawls 80 and 81 extend upward and forward from their respective pivot pins 82 and 83.

As seen in FIG. 3, the low force pawl 80 is relatively short, extends upward and forward at a substantial angle to the horizontal, here at about 45° to 55° off horizontal and has a forward rack engaging end which is tapered so that its forward upper edge subtends about a 60° angle. In contrast, the high force drive pawl 81 is relatively long, extends forward and upward at a shallower angle to the horizontal, here at about 25° to 35° off horizontal, and has a forward rack engaging end squared off so that its forward and upper edge subtends about a 90° angle. The result is that the forward upper edges of the pawls 80 and 81 abut rear tooth faces of the rod 50, as seen in the rest position of the trigger 70 in FIG. 3, near the root and with area or substantially area contact, for best transfer of forward force from the respective pawl to the rear face of the corresponding tooth.

The distance from pivot axis to upper front tooth engaging edge for the high force pawl 81 is about twice that for the low force pawl 80.

Respective support pins 84 and 85 (FIG. 2 and 3) extend across the trigger groove 75 and each have opposite ends fixed in the laterally spaced cheeks 76 of the trigger head 74. Hairpin springs 86 and 87 (coil springs with extended ends) are, as seen in FIGS. 2 and 3, sleeved on the respective support pins 84 and 85. The hairpin spring 86 has legs resiliently pressed toward each other between the underside of the low force pawl 80 and the bottom 91 of the trigger head groove 75 so as to resiliently press the forward upper edge of the low force pawl 80 up against the bottom of the rod 50. Similarly, the hairpin spring 87 has ends resiliently pressed between the underside of the high force pawl 81 and the bottom 91 of the trigger head groove 75 so as to press the forward upper edge of the high force pawl 81 up against the bottom of the rod 50. In this way, when the rod 50 is rotated into its position shown in FIG. 3, with the rack teeth 54 facing downward, the front upper edges of the pawls 80 and 81 are resiliently pressed up into engagement with series of teeth 54 on the underside of the rod 50.

Pulling rearward the trigger 70 from its solid position toward its dotted line position in FIG. 3 pivots the trigger head 74 clockwise about its pivot pin 71 and thus pivots forwardly and somewhat upwardly the pawl support pins 82 and 83, in turn displacing forward the pawls 80 and 81 from their solid line rest positions shown. With both pawls in contact with the rack teeth 54, the low force pawl 80 advances forward further than the high force pawl 81 as the trigger 70 is pulled rearward by the user. Accordingly, the low force pawl 80 advances the rod 50 forwardly farther than the top front edge of the high force pawl 81 advances, such that the low force pawl 80 controls the forward advancement of the rod 50 and one or more rack teeth 54 skip forwardly past the top front edge of the high force pawl 81 during a complete pull of the trigger 70.

However, structure is provided for allowing the high force pawl 81 to control forward advancement of the rack rod 50. More particularly, a switch lever 92 (FIGS. 2 and 3) is pivoted at its rear end on a pin 93 fixedly but rotatably supported on the left half (looking forward) 17L of the body 17. The switch lever 92 extends forward and somewhat upward from the pivot pin 93 past and behind (as seen in FIG. 3) the upper end of the low force pawl 80. The low force pawl 80 has a pushdown pin 94 fixedly extending leftwardly (looking forward) therefrom, along the underside of the switch lever 92 near its pivot pin 93. Thus, downward pivoting of the switch lever 92 (clockwise pivoting in FIG. 3) downwardly displaces the pushdown pin 94 and thereby clockwise (FIG. 3) pivots the low force pawl 80 down out of its FIG. 3 contact with the rack teeth 54 of the rod 50 to its downward position shown in FIG. 5, in which the low force pawl 80 is out of contact with the teeth 54 of the rod 50 and only the high force pawl 81 remains in contact with the rack teeth 54 of the rod 50. With only the high force pawl 81 still in driving contact with the rack teeth 54, one full pull of the trigger 70 forward advances the ram disk 52 through a relatively small displacement but at a relatively high forwardly directed force, as contrasted to the larger displacement and smaller force achievable by the low force pawl 80 when it engages the rack teeth 54.

The forward portion 95 of the switch lever 92 is in the form of a circular cross section, reduced width (diameter) forward extension of the rear portion 96 of the switch lever. The rear portion 96 is of square cross section to form a forwardly facing shoulder where it joins the forward portion 95. An elongate coil compression spring 100 is snugly but slidably sleeved over the forward portion 96 of the switch lever 92 and at its rear end abuts such shoulder formed by the rear portion 96 of the switch lever, such that the latter fixedly backs the coil spring 100.

A control shaft 101 (FIGS. 2 and 3) has an enlarged cylindrical head 102 having a diametral hole therethrough slidably but snugly receiving the cylindrical forward portion 95 of the switch lever 92 at a location forward of the coil spring 100. Thus, the coil spring 100 is trapped axially between the control shaft head 102 and the rear portion 96 of the switch lever 92. The control shaft 100 has a shank 103 of reduced diameter which extends leftward (FIG. 2) from the head 102, snugly but slidably through a vertically elongate slot 104 which extends transversely through the thickness of the leftward half 17L of the gun body 17. The shank 103 extends outside the body 17 far enough to receive thereon a washer 105 (FIG. 2) and a knob 106. In the embodiment shown, the knob is fixed on the outer end of the shank 103 by a screw 107 (FIG. 3).

The slot 104 is substantially kidney bean shaped in the sense of having forward extending recesses 110 (FIGS. 2 and 5) at the top and bottom thereof, separated by a vertically intermediate, rearward protruding land 111. The upstanding rear edge of the slot 104 is substantially straight. Accordingly, the land 111 and the spring 100 together define a resilient detent mechanism wherein the spring 100 tends to forwardly push the shank 103 of the control shaft 101 forwardly into the adjacent top or bottom recess 110 when the control shaft is at the top or bottom of the slot 104, so that the control shaft 101 is resiliently urged to stay in either the top or bottom of the slot 104. On the other hand, a manual up or down push on the knob 106 is sufficient to overcome the spring detent defined by the land 111 and spring 100 and displace the control shaft 101 to the other end of the slot 104.

Thus, with the knob 106 in its up position, at the top of the slot 104, the switch lever 92 in its up position shown in FIG. 3 and allows the low force pawl 80 to engage the rack teeth 54 of the rod 50 and thereby control forward displacement of the ram disk 52. On the other hand, with the knob 106 in its down position, the low force pawl 80 is held in its lowered position shown in FIG. 5, out of contact with the rack teeth 54 of the rod 50, such that the high force pawl 81 controls forward displacement of the ram disk 52.

To automatically return the trigger 70 to its forward, rest, solid line position of FIG. 3, after a rearward pull toward its rearward dotted line position, a pair of coil tension springs, disposed side-by-side as seen at 120, are connected to and between the high force pawl pivot pin 82 (FIG. 3) and a transverse pin 121 fixed to and extending between the two transversely opposed halves of the body 17. More particularly, the spring attachment pin 121 is located at the lower rear corner of the receiver 20 behind and below the low force pawl pivot pin 82 and behind the trigger head 74 and the joinder of the handle 21 to the receiver 20. The forward, upper ends of the springs 120 are conveniently received in a rearward and downward opening slot 122 in the rear (bottom) end of the low force pawl 80, in which the middle portion of the pivot pin 82 is exposed to enable hooking of the forward ends of the spring 120 therearound. Since the ends of the pin 82 are fixed in the cheeks 75 of the trigger head 74, the spring 120 thus pulls the trigger 70 in a counterclockwise direction toward its forward position shown in solid line in FIG. 3, after each manual rearward pull on the trigger 70.

A non-return pawl 130 (FIGS. 2 and 4) is pivoted at its rear, lower end on a pivot pin 131 fixed to and extending transversely between the left and right halves of the body 17, and more particularly between the halves of the receiver 20. The non-return pawl 130 extends upward and forward from the pivot pin 131 and has an upward forward corner defining an acute angle as seen from the side in FIG. 4, much like that of the upper, forward end of the low force pawl 80 above described. The shape of the upper forward edge of the non-return pawl 130 is similarly shaped, as seen from the side, to conform with the shape of the rack teeth 54 of the rod 50 and, more particularly, to ride solidly, in area contact, with the rear face of the adjacent rack tooth 54. A hairpin spring 132 is wrapped around the pivot pin 131 at its lower rear end and bears upward and rearward against the rear wall 40 of the receiver 20 and at its forward upper end bears against the underside of the non-return pawl 130, ahead of the pivot pin 131, to urge the upper front edge of the non-return pawl 130 into engagement with the rear face of the adjacent rack tooth 54 (FIG. 4) of the rod 50, when such rack teeth 54 face downward, to prevent rearward movement of the rod 50. This prevents rearward movement of the ram disk 52 and cartridge piston 61 in response to rearward pressure thereon from the bone cement 14 in the cartridge 12.

In the embodiment shown, the hairpin spring 132 is generally U-shaped as seen from the top in FIG. 2, having a transverse bight 133 at its upper forward end, underlying the central portion of the non-return pawl 130, and having left and right legs 134 and 135 which transversely sandwich the non-return pawl 130, wrap around the corresponding pivot pin 131, and have rear ends transversely spaced from each other and bearing against the rear receiver wall 40 as seen in FIG. 4.

The hairpin springs 86 and 87 which upwardly urge the low force and high force pawls 80 and 81 may also be similarly U-shaped, with bights underlying and bearing against the underside of the low force and high force pawls 80 and 81. Alternatively, the springs 86 and 87 may simply be single leg hairpin springs as indicated in dotted lines in FIG. 8.

OPERATION

Although the operation of the apparatus has been generally set forth above, same is briefly summarized below for convenient reference.

The gun 11 is conveniently assembled by mounting the various internal parts with respect to the inside of the left half 17L of the body 17 and then securing the right half 17R thereto by the screws 22. The cartridge support 23 can then be fixed to the front of the receiver 20 by the screws 24 and the ram disk 52 can be fixed to the front end of the ram rod 50 by the screw 1.

With the gun 11 thus assembled, the rear end of a cartridge 12, loaded with bone cement, can be dropped into the main recess 25 of the cartridge support 23 (compare the cartridge positions in FIGS. 3 and 4) so that the cartridge rear flange 30 is blocked by the front flange 27 of the cartridge support 23 from forward movement with respect to the gun 11. During installation of the cartridge 12 on the gun 11, the rod 50 is in its rearward position, so that its ram disk 52 is entirely recessed in the secondary recess 35 of the cartridge support 23 and thus is out of the main recess 25, as seen in FIG. 3, and hence out of the way of dropping thereinto the rear end portion of the cartridge 12.

The rod 50 can be slid to its rearward position, and indeed can be slid rearwardly to any extent desired, by rotating it about its length axis so that its rack teeth 54 no longer point downwardly and engage the pawls 80, 81 and 130. For example, with the hand grip 53 and teeth 54 pointed away from the pawls so that the pawls can no longer engage the rack teeth 54, the pawls instead simply bear slidably against the smooth surface of the upper or side faces of the ram rod 50.

The cartridge 12 can be loaded with bone cement 14 in any desired manner. However, it is particularly advantageous that the bone cement cartridge 12 be loaded with bone cement in the manner shown in copending U.S. application Ser. No. 07/769004, assigned to the assignee of the present invention. The latter minimizes the opportunity for gas or air bubbles in the bone cement in the cartridge 12. Such bone cement is typically mixed from two components, which upon mixing begin to cure from a low viscosity, relatively free flowing liquid, like a thin pancake batter, to a substantially less flowable, puttylike character. The cement may indeed be in such harder, puttylike consistency as its injection into the bone cavity at the surgical site is being completed. Eventually the cement hardens to a rigid state, within the bone cavity for anchoring a prosthesis (such as a hip prosthesis) not here shown.

In view of the increasing viscosity (lessening flowability) of such bone cement in the few minutes available for injection into the bone cavity and following mixing, the gun 11 is preferably operated as follows.

With the rod 50 in its tooth downward position shown in FIG. 4, and the knob 106 (FIG. 2) in its up position (the control shaft 102 is in its up position illustrated in FIG. 4) the low force high displacement pawl 80 engages the rack teeth 54 (as does the high force pawl 81. Pulling the trigger 70 rearward toward its dotted line position of FIG. 3, clockwise pivots the trigger head 74 and the low force pawl 80, to rightwardly advance the rod 50, ram disk 52 and cartridge piston 61 and thereby impel bone cement 14 out of the front end of the cartridge 12, through the nozzle 13 and tip 15 and into the cavity of the femur 16 (in the particular example shown in FIG. 1) to start filling same with bone cement 14.

Due to its easy initial flowability, the bone cement 14 can be pushed forward by the low force pawl 80 in relatively large forward displacements of the piston 61 in a series of pulls (from forward to rearward positions) of the piston 70, without requiring the operator to exert excessive force on the trigger 70. The cavity of the femur 16 (in the particular example shown) can thus be filled to near its full capacity very quickly and at a relatively high flow rate with this relatively easily flowable bone cement 14.

However, as this injection of bone cement continues, the bone cement continues curing and becomes less and less flowable. Typically then in the last stage of filling of the femur 16, the bone cement 14 has become at least somewhat less flowable and somewhat harder to push forwardly out of the cartridge 12 and into the cavity of the femur 16. Further, during the last stage of injection of bone cement into the femur, it may be desired to exert greater pressure on the cement so as to cause it to seat more firmly in the pores in the bone surface surrounding the cavity in the femur 16. For either or both reasons, it may thus be desired by the operator to exert a greater forward force on the cartridge piston 61 for a given rearward pulling force (hand force) on the trigger 70.

The operator achieves this desire by pushing down the knob 106 (FIG. 2), and hence the control shaft head 102 and switch lever 92, from their upper FIG. 4 position to their lower FIG. 5 position. In this lower position, the switch lever 92 pushes downward the upper front edge of the low force pawl 80 out of contact with the ram teeth 54 on the underside of the rod 50. Accordingly, only the high force pawl 81 is left in contact with the ram teeth 54 of the rod 50. Accordingly, further operator pulls on the trigger 70 push the piston 61 forwardly through substantially smaller displacements but at substantially higher force to apply more pressure to the bone cement entering the femur cavity. If desired to make more effective use of this higher force on the piston 62, the tip 15 (FIG. 1) can be removed and substituted by a tip of any convenient form to close off the entrance to the femur cavity (except to the flow from the cartridge 12) and thereby block leakage of pressurized bone cement out of the open end of the femur cavity around the cartridge tip.

When injection of bone cement is completed, the cartridge 12, with its tip (tip 15 or some other tip), can be removed from the gun 11, by a reversal of its installation step above described, and discarded. Also, the rod 50 can be rotated to its tooth up position not shown and pulled rearward to its FIG. 3 position and the used cartridge 12 can be removed from the gun 11. The gun 11 then is ready for another use, with a fresh bone cement cartridge 12. The gun 11 can be sterilized conventionally for use with another patient.

Figure 10:
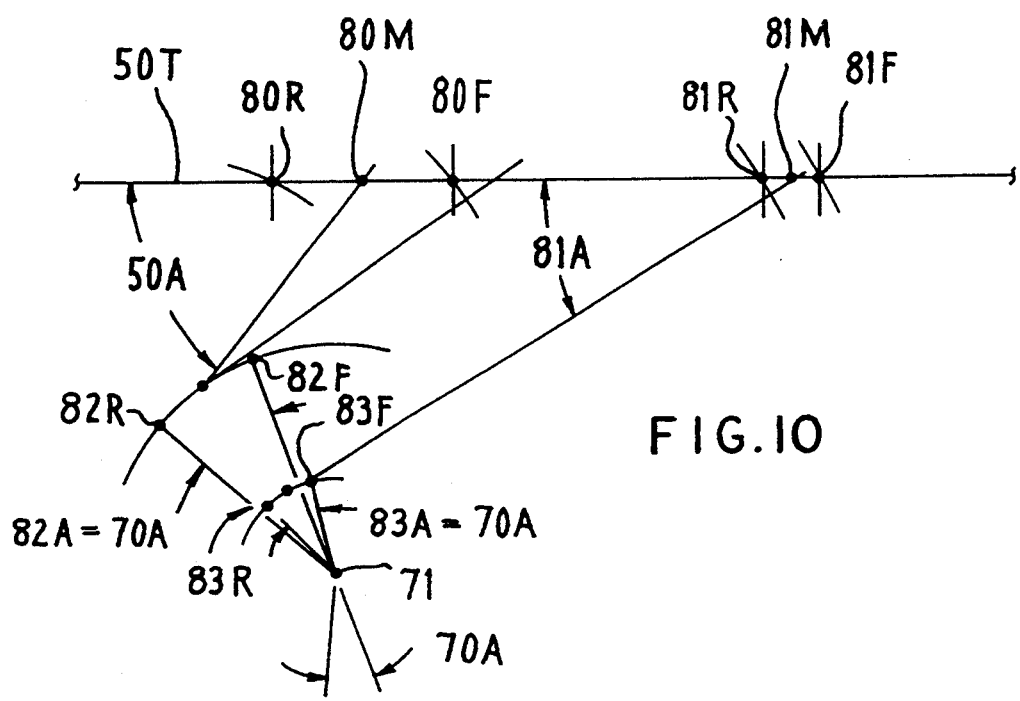
FIG. 10 is a line diagram which shows the angle traversed by a full displacement of the trigger and the corresponding displacement start and end points of the pivot axis and rod engagement point for each of the low force and high force pawls and thereby the amount of displacement of the rod by the high force and low force pawls during a full trigger pull, in the embodiment of FIG. 3.

FIG. 10 diagrammatically compares the operation of the pawls 80 and 81. In FIG. 10 the horizontal line 50T represents the mid-height of the rack teeth 54 on the underside of the rod 50 in its orientation of FIG. 4.

As shown diagrammatically in FIG. 10, a full pull of the trigger 70 pivots the upper portion of the trigger head 74 clockwise through an angle 70A and therewith pivots the pivot pins 82 and 83 of the low force and high force pawls through identical angles 82A and 83A from corresponding rearward positions 82R and 3R to corresponding forward positions 82F and 83F. This advances the ram tooth engaging, upper and forward edges of the low force and high force pawls 80 and 81 from respective rear positions 80R and 81R to respective forward positions 80F and 81F. As seen in FIG. 10, the single trigger pull displacement of the rod 50 under the control of the low force pawl 80 would be from position 80R to position 80F. On the other hand, the forward displacement of the rod 50, under control of the high force pawl 81, would be from position 81R to 10 position 81F. The cartridge piston 62 of course goes through the same forward displacement as the rod 50 pushing it. Accordingly, it will be seen that the piston displacement achieved by the low force pawl 80 is about four times that achieved by the high force pawl 81.

From the geometry of FIG. 10, it can be seen that the forwardly directed force applied to the rod 50 and hence to the ram plate 52 and piston 61, the high force pawl 81 is here several times (nearly three times) the amount of forward force applied to the piston by the low force pawl 80.

More particularly, the low force pawl pivot axis (pin 82 axis) is more than twice the distance to the axis of the handle pivot pin 71 than is the axis of the pivot pin 83 of the high force pawl. Further, at the middle of the displacement of the handle 70, the high force pawl 81 extends at virtually a right angle to the pivot radius between the axes of its pivot pin 83 and the handle pivot pin 71, whereas the low force pawl is roughly 20° off that orientation such that a portion of the force applied to the low force pawl pivot pin 82R by pulling of the trigger 70 is not applied to forward the piston 61. Further, the elongate high force pawl extends at an average angle to the rod 50 of about 30°, so as to apply to the rod 50 a larger proportion of the force of the clockwise advancing pivot pin 83 (during a pull of the trigger 70) than is applied to the rod 50 by the pivot pin 82 acting through the low force pawl 80, due to the larger average angle of about 50° between the low force pawl 80 and the rod 50.

Thus, a number of factors contribute to the several times higher force applied to the piston 61 by the high force pawl 81, as compared to the low force pawl 80, by a given pull of the trigger 70.

For convenience in the above discussion of FIG. 10, the midpoint in the forward displacement of the respective forward upper edges of the pawls 80 and 81 are indicated respectively at 80M and 81M in FIG. 10.

The gun 11 is preferably constructed of stainless steel or equivalent other inert, strong and rigid material capable of being sterilized for reuse in additional surgical procedures over a long period of time.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. Apparatus for injecting bone cement for a cartridge in orthopedic surgery, comprising:
   a body;
   means for supporting a bone cement containing cartridge on said body;
   trigger means actuable for movement on said body;
   ram means advanceable on said body in response to actuation of said trigger means for forcing bone cement from said cartridge to a surgical site;
   means operatively interposed between said trigger means and ram means and actuable for changing, between a lower force value and a higher force value, the force applicable by said ram means to the cartridge in response to a given actuation of said trigger means, in which said force changing means comprises first and second ram advancing means alternatively selectable for applying a lower force and a higher force to said ram means, and switch means actuable to select between said first and second ram advancing means.

2. The apparatus of claim 1 in which said force changing means includes means for changing, between a higher volume and a lower volume, the volume of bone cement forced from said cartridge by said given trigger means actuation.

3. The apparatus of claim 2 in which said force changing means has first and second alternative positional states, said first state corresponding to said lower force value and said higher volume, said second state corresponding to said higher force value and said lower volume.

4. The apparatus of claim 1 in which said ram means includes an elongate rod axially movable on said body, said first and second ram advancing means being engaged with said rod for advancing said rod and thereby forcing bone cement from a cartridge.

5. The apparatus of claim 1 in which said first and second ram advancing means are mounted on said trigger means, said switch means being accessible outside said body for placing at least one of said first and second ram advancing means out of force applying relation with said ram means.

6. The apparatus of claim 1 in which said trigger means is pivotable on an axis on said body, said first and second ram advancing means being mounted on said trigger means at locations respectively closer to and further from said pivot axis of said trigger means.

7. Apparatus for injecting bone cement from a cartridge in orthopedic surgery, comprising:
   a body;
   means for supporting a bone cement containing cartridge on said body;
   trigger means actuable for movement on said body;
   ram means advanceable on said body in response to actuation of said trigger means for forcing bone cement from said cartridge to a surgical site;
   means operatively interposed between said trigger means and ram means and actuable for changing, between a lower force value and a higher force value, the force applicable by said ram means to the cartridge in response to a given actuation of said trigger means, in which said ram means comprises an elongate rod advanceable towards the cartridge and having a series of rear facing teeth distributed longitudinally thereon, said trigger means having a head advanceable toward said cartridge, said interposed means comprising a low force pawl and a high force pawl pivotable on said head and extending up and forward into forward driving contact with said teeth for forwardly advancing said rod upon forward movement of said head.

8. The apparatus of claim 7 including switch means actuable to separate said low force pawl from said teeth for forwarding of said rod by said high force pawl.

9. The apparatus of claim 8 in which said switch means comprises a lever pivotable on said body and resilient detent means manually overcomeable for shifting said lever from an enabling position, out of operative contact with said low force pawl and leaving the low force pawl in driving contact with said teeth on said rod, to a disabling position, displacing said low force pawl out of contact with said teeth on said rod.

10. The apparatus of claim 9 in which said resilient detent means comprises a slot in said body having enlarged ends, knob means movable along said lever and out of said body through said slot, and resilient means interposed between said lever and knob means for urging said knob means transverse of said slot into said enlarged slot ends to resiliently resist shifting said knob means along said slot from one enlarged end to the other.

11. The apparatus of claim 7 in which said trigger means has a pivot axis on said head, said low force pawl comprising a relatively short pawl pivoted on said head on an axis remote from said trigger means pivot axis and engaging said rod teeth at a relatively large acute angle, said high force pawl comprising a relatively long pawl pivoted on said head on an axis closer to said trigger means pivot axis and engageable with said rod teeth at a relatively smaller acute angle, so as to provide a relatively shorter stroke and larger mechanical advantage to the high force pawl as compared to the low force pawl, said high force pawl thereby having a larger ram force per increment of force on said trigger means.

12. Apparatus for injecting bone cement from a cartridge in orthopedic surgery, comprising:
a body;
means for supporting a bone cement containing a cartridge on said body;
trigger means actuable for movement on said body;
a rod advanceable on said body in response to actuation of said trigger means for forcing bone cement from said cartridge to a surgical site, said rod having a series of rear facing teeth thereon, said trigger means having a pivot axis, said trigger means having a head carrying said trigger means pivot axis;
a low force pawl comprising a relatively short pawl pivotable on said head on an axis remote from said trigger means pivot axis and engaging said rod teeth at a relatively large acute angle;
a high force pawl comprising a relatively long pawl pivoted on said head on an axis closer to said trigger means pivot axis and engaging said rod teeth at a relatively smaller acute angle, so as to provide a relatively shorter stroke and larger mechanical advantage to the high force pawl as compared to the low force pawl and so as to provide a larger ram force per increment of force on the trigger means from said high force pawl.

13. The apparatus of claim 12 including spring means simultaneously urging the high force pawl and the low force pawl against said teeth on said rod and switch means manually actuable to disengage said low force pawl from said teeth on said rod.

14. The apparatus of claim 12 in which said high force pawl is located on said trigger means head at a location forward of said low force pawl.

15. The apparatus of claim 12 including a non-return pawl pivotable on said body and engageable with said teeth on said rod for blocking unintended return of said rod rearward, as due to pressure of bone cement in a cartridge.

16. The apparatus of claim 15 including spring means on said head for urging said low force pawl and high force pawl against said teeth on said rod and further spring means on said body for urging said non-return pawl against said teeth on said rod.

17. The apparatus of claim 12 including a pin defining the pivot axis of said low force pawl, said low force pawl having a rear facing slot exposing said pin, spring means extending rearward from said pin to a rear end at a fixed location on said body behind said trigger means for biassing said trigger means to a forward rest position, said trigger means comprising a lever-like member pivotable on said body below said pawls such that rearward displacement of the lower end of said lever-like member forwards said pawls against said teeth of said rod for extruding bone cement forward out of the cartridge.

18. The apparatus of claim 12 including switch means actuable to separate said low force pawl from said teeth for forwarding of said rod by said high force pawl, said switch means comprising a lever pivoted on said body and resilient detent means manually overcomeable for shifting said lever from an enabling position, out of operative contact with the low force pawl for leaving the latter in driving contact with said teeth on said rod, to a disabling position displacing said low force pawl out of operative contact with said teeth on said rod.

19. The apparatus of claim 18 in which said resilient detent means comprises a slot in said body having enlarged ends, knob means movable along said lever and extending out of said body through said slot for manual engagement, and resilient means interposed between said lever and knob means for urging said knob means transverse of said slot into said enlarged slot ends to resiliently resist shifting of said knob means along said slot from one enlarged end to the other.

20. Apparatus for injecting bone cement from a cartridge in orthopedic surgery, comprising:
a body;
a bone cement containing cartridge supportable on a forward portion of said body, said cartridge having a forward extending shell and a radially outward extending flange on a rear end portion thereof;
trigger means actuable for movement on said body;
ram means advanceable on said body for forcing bone cement from said cartridge to a surgical site;
means operatively interposed between said trigger means and ram means and responsive to actuation of said trigger means for advancing said ram means;
cartridge support means for removably fixing said cartridge in forward extending relation on said body ahead of said ram means, said cartridge support means having a radially opening recess for receiving said cartridge flange and guard flange means partly blocking the front end of said recess on three sides thereof to guard against forward escape of said cartridge flange from said recess while said ram means forces bone cement from said cartridge to a surgical site, said guard flange means being open on one side for receiving said shell thereinto during insertion of said cartridge flange in said recess, and resilient detent means operatively associated with said guard flange means near the open side thereof for resiliently blocking unintended escape of said cartridge from said cartridge support means.

21. The apparatus of claim 20 in which said resilient detent means comprises opposed ears on said guard flange flanking the open side thereof and a portion of said shell adjacent said cartridge flange resiliently impressible by said ears upon entry and exit of said cartridge with respect to said cartridge support means.

22. Apparatus for injecting bone cement from a cartridge in orthopedic surgery, comprising:
 a body;
 means for supporting a bone cement containing cartridge on said body;
 a trigger actuable for movement on said body; a ram advanceable on said body in response to actuation of said trigger for forcing bone cement from said cartridge to a surgical site;
 first force applying means responsive to a preselected force on said trigger for applying a first force to said ram so as to inject an initial charge of cement into a surgical site at a first pressure;
 second force applying means responsive to the same preselected force on said trigger for applying a second and higher force to said ram so as to inject a smaller final charge of cement into such surgical site at a second pressure substantially higher than said first pressure;
 switch means actuable for substituting said second force applying means in place of said first force applying means.

23. The apparatus of claim 22 in which said first force applying means has a substantially longer ram stroke/trigger displacement ratio than said second force applying means, to enable the apparatus to more rapidly inject more cement into the surgical site by use of said lower pressure first force applying means than by use of said higher pressure second force applying means.

24. Apparatus for injecting bone cement from a cartridge in orthopedic surgery, comprising:
 a body;
 means for supporting a bone cement containing cartridge on said body;
 a trigger actuable for movement on said body;
 a ram advanceable on said body in response to actuation of said trigger for forcing bone cement from said cartridge to a surgical site;
 means operatively interposed between said trigger and ram and actuable for (1) first displacing a relative large quantity of cement at a relatively low pressure into said surgical site to mostly fill the surgical site upon completion thereof, and (2) secondly displacing a smaller final quantity of cement at a substantially higher pressure into said surgical site to complete the filling of the surgical site;
 said operatively interposed means comprising first and second coupling means alternatively interposed operatively between said trigger and ram for respectively carrying out said first and second displacing and substituting means actuable for substituting said first coupling means for said means coupling means.

25. Apparatus for injecting bone cement from a cartridge in orthopedic surgery, comprising:
 a body;
 means for supporting a bone cement containing cartridge on said body;
 a trigger displaceable on said body;
 a ram advanceable on said body in response to actuation of said trigger for forcing bone cement from the cartridge to a surgical site;
 means operatively interposed between said trigger and ram and actuable for changing the length displacement of the ram, from a higher displacement range to a lower displacement range, to be effected by the same length of displacement of the trigger such that the displacement range of the ram can be changed without lengthening or shortening the displacement range of the trigger, said displacement changing means comprising first and second ram advancing means alternatively selectable for respectively displacing said ram a greater distance and a lesser distance in response to the same displacement of said trigger, and switch means actuable to select between said first and second ram advancing means.

* * * * *

UNITED STATES PATENT AND TRADEMARK OFFICE
CERTIFICATE OF CORRECTION

PATENT NO. : 5 431 654
DATED : July 11, 1995
INVENTOR(S) : David M. NIC

It is certified that error appears in the above-indentified patent and that said Letters Patent is hereby corrected as shown below:

```
Column 12, line 1; change "for" to ---from---.(second occurrence)
Column 13, line 41; delete "a" (second occurrence).
Column 15, line 19; after "body;" begin a new paragraph.
Column 16, line 20; change "means" (second occurrence)
                    to ---second---.
```

Signed and Sealed this

Seventeenth Day of October, 1995

Attest:

BRUCE LEHMAN

Attesting Officer

Commissioner of Patents and Trademarks